United States Patent [19]
Conlon et al.

[11] Patent Number: 5,945,401
[45] Date of Patent: Aug. 31, 1999

[54] PEPTIDE ANALOGUES OF THE 65KD ISOFORM OF HUMAN GLUTAMIC ACID DECARBOXYLASE AND USES THEREOF

[76] Inventors: Paul J. Conlon, 450 Santa Dominga, Solana Beach, Calif. 92075; Nicholas Ling, 5324 Bloch St., San Diego, Calif. 92121; Amitabh Gaur, 12570 Picrus St., San Diego, Calif. 92129; R. David G. Leslie, 24 Bramerton St., London, United Kingdom, SW3 5LA; Marco Londei, 3 Prebend Mansions Chiswick High Rd., London, United Kingdom, W4 2LU

[21] Appl. No.: 08/494,624

[22] Filed: Jun. 23, 1995

[51] Int. Cl.⁶ ..................................................... A61K 38/43
[52] U.S. Cl. ............................ 514/14; 530/323; 530/326; 530/327; 530/329
[58] Field of Search .................................. 530/300, 326, 530/327, 323, 329; 514/2, 14

[56] References Cited

U.S. PATENT DOCUMENTS

| | | | |
|---|---|---|---|
| 5,041,380 | 8/1991 | Ruoslahti et al. | 435/325 |
| 5,674,978 | 10/1997 | Tobin et al. | 530/326 |

FOREIGN PATENT DOCUMENTS

| | | |
|---|---|---|
| WO 95/07464 | 3/1995 | WIPO . |
| WO 95/07992 | 3/1995 | WIPO . |

OTHER PUBLICATIONS

Guery et al. Critical Rev. Immunol. 13, 195–206, 1993.
Chicz et al. Immunol. Today 15, 155–160, 1994.
Evavold et al. Immunol. Today 14, 602–609, 1993.
Schon et al. J. Bacteriol. 175, 2465–2469, 1993.
Chen et al., "Responses of NOD Congenic Mice to a Glutamic Acid Decarboxylase–derived Peptide," *Journal of Autoimmunity* 7: 635–641, 1994.
Karlsen et al., "Cloning and primary structure of a human islet isoform of glutamic acid decarboxylase from chromosome 10," *Proc. Natl. Acad. Sci. USA* 88: 8337–8341, 1991.
Kaufman et al., "Spontaneous loss of T–cell tolerance to glutamic acid decarbaoxylase in murine insulin–dependent diabetes," *Nature* 366: 69–72, 1993.
Li et al., "Indentification of Autoantibody Epitopes of Glutamic Acid Decarboxylase in Stiff–Man Syndrome Patients," *Journal of Immunology* 152(2): 930–934, 1994.
Lohmann et al., "Immunodominant epitopes of glutamic acid decarboxylase 65 and 67 in insulin–dependent diabetes mellitus,"*The Lancet*343(8913): 1607–1608, 1994.
Quinn and Sercarz, "T Cells with Multiple Fine Specificities are Used by Non–obese Diabetic (NOD) Mice in the Response to GAD (524–543),"*Journal of Autoimmunity*9: 365–370, 1996.
Saï et al., "Immunization of non–obese diabetic (NOD) mice with glutamic acid decarboxylase–derived peptide 524–543 reduces cyclophosphamide–accelerated diabetes," *Clin. Exp. Immunol* 105: 330–337, 1996.

*Primary Examiner*—Prema Mertz

[57] ABSTRACT

Peptides and peptide analogues of the 65 kD isoform of human glutamic acid decarboxylase are provided for use in the treatment and prevention of diabetes. Peptide analogues contain generally from one to three amino acid alterations. Peptides and analogues may be used to diagnose diabetes and detect a predisposition to diabetes.

28 Claims, 4 Drawing Sheets

```
AGCTCGCCCGCAGCTCGCACTCGCAGGCGACCTGCTCCAGTCTCCAAAGCCGATGGCATCTCCGGGCTCTGGCTTTTGGT   80
                                                          M  A  S  P  G  S  G  F  W    9

CTTTCGGGTCGGAAGATGGCTCTGGGGATTCCGAGAATCCCGGCACAGCGCGAGCCTGGTGCCAAGTGGCTCAGAAGTTC  160
 S  F  G  S  E  D  G  S  G  D  S  E  N  P  G  T  A  R  A  W  C  Q  V  A  Q  K  F   36

ACGGGCGGCATCGGAAACAAACTGTGCGCCCTGCTCTACGGAGACGCCGAGAAGCCGGCGGAGAGCGGCGGGAGCCAACC  240
  T  G  G  I  G  N  K  L  C  A  L  L  Y  G  D  A  E  K  P  A  E  S  G  G  S  Q  P   63

CCCGCGGGCCGCCGCCCGGAAGGCCGCCTGCGCCTGCGACCAGAAGCCCTGCAGCTGCTCCAAAGTGGATGTCAACTACG  320
   P  R  A  A  A  R  K  A  A  C  A  C  D  Q  K  P  C  S  C  S  K  V  D  V  N  Y    89

CGTTTCTCCATGCAACAGACCTGCTGCCGGCGTGTGATGGAGAAAGGCCCACTTTGGCGTTTCTGCAAGATGTTATGAAC  400
 A  F  L  H  A  T  D  L  L  P  A  C  D  G  E  R  P  T  L  A  F  L  Q  D  V  M  N   116

ATTTTACTTCAGTATGTGGTGAAAAGTTTCGATAGATCAACCAAAGTGATTGATTTCCATTATCCTAATGAGCTTCTCCA  480
  I  L  L  Q  Y  V  V  K  S  F  D  R  S  T  K  V  I  D  F  H  Y  P  N  E  L  L  Q  143

AGAATATAATTGGGAATTGGCAGACCAACCACAAAATTTGGAGGAAATTTTGATGCATTGCCAAACAACTCTAAAATATG  560
   E  Y  N  W  E  L  A  D  Q  P  Q  N  L  E  E  I  L  M  H  C  Q  T  T  L  K  Y   169

CAATTAAAACAGGGCATCCTAGATACTTCAATCAACTTTCTACTGGTTTGGATATGGTTGGATTAGCAGCAGACTGGCTG  640
  A  I  K  T  G  H  P  R  Y  F  N  Q  L  S  T  G  L  D  M  V  G  L  A  A  D  W  L  196

ACATCAACAGCAAATACTAACATGTTCACCTATGAAATTGCTCCAGTATTTGTGCTTTTGGAATATGTCACACTAAAGAA  720
  T  S  T  A  N  T  N  M  F  T  Y  E  I  A  P  V  F  V  L  L  E  Y  V  T  L  K  K  223

AATGAGAGAAATCATTGGCTGGCCAGGGGGCTCTGGCGATGGGATATTTTCTCCCGGTGGCGCCATATCTAACATGTATG  800
   M  R  E  I  I  G  W  P  G  G  S  G  D  G  I  F  S  P  G  G  A  I  S  N  M  Y   249

CCATGATGATCGCACGCTTTAAGATGTTCCCAGAAGTCAAGGAGAAAGGAATGGCTGCTCTTCCCAGGCTCATTGCCTTC  880
 A  M  M  I  A  R  F  K  M  F  P  E  V  K  E  K  G  M  A  A  L  P  R  L  I  A  F   276

ACGTCTGAACATAGTCATTTTTCTCTCAAGAAGGGAGCTGCAGCCTTAGGGATTGGAACAGACAGCGTGATTCTGATTAA  960
 T  S  E  H  S  H  F  S  L  K  K  G  A  A  A  L  G  I  G  T  D  S  V  I  L  I  K   303

ATGTGATGAGAGAGGGAAAATGATTCCATCTGATCTTGAAAGAAGGATTCTTGAAGCCAAACAGAAAGGGTTTGTTCCTT 1040
   C  D  E  R  G  K  M  I  P  S  D  L  E  R  R  I  L  E  A  K  Q  K  G  F  V  P   329

TCCTCGTGAGTGCCACAGCTGGAACCACCGTGTACGGAGCATTTGACCCCCTCTTAGCTGTCGCTGACATTTGCAAAAAG 1120
 F  L  V  S  A  T  A  G  T  T  V  Y  G  A  F  D  P  L  L  A  V  A  D  I  C  K  K  356

TATAAGATCTGGATGCATGTGGATGCAGCTTGGGGTGGGGGATTACTGATGTCCCGAAAACACAAGTGGAAACTGAGTGG 1200
 Y  K  I  W  M  H  V  D  A  A  W  G  G  G  L  L  M  S  R  K  H  K  W  K  L  S  G  383
```

*Fig. 1A*

```
CGTGGAGAGGGCCAACTCTGTGACGTGGAATCCACACAAGATGATGGGAGTCCCTTTGCAGTGCTCTGCTCTCCTGGTTA   1280
  V  E  R  A  N  S  V  T  W  N  P  H  K  M  M  G  V  P  L  Q  C  S  A  L  L  V     409

GAGAAGAGGGATTGATGCAGAATTGCAACCAAATGCATGCCTCCTACCTCTTTCAGCAAGATAAACATTATGACCTGTCC   1360
 R  E  E  G  L  M  Q  N  C  N  Q  M  H  A  S  Y  L  F  Q  Q  D  K  H  Y  D  L  S   436

TATGACACTGGAGACAAGGCCTTACAGTGCGGACGCCACGTTGATGTTTTTAAACTATGGCTGATGTGGAGGGCAAAGGG   1440
 Y  D  T  G  D  K  A  L  Q  C  G  R  H  V  D  V  F  K  L  W  L  M  W  R  A  K  G   463

GACTACCGGGTTTGAAGCGCATGTTGATAAATGTTTGGAGTTGGCAGAGTATTTATACAACATCATAAAAAACCGAGAAG   1520
  T  T  G  F  E  A  H  V  D  K  C  L  E  L  A  E  Y  L  Y  N  I  I  K  N  R  E    489

CGTTTCTCCATGCAACAGACCTGCTGCCGGCGTGTGATGGAGAAAGGCCCACTTTGGCGTTTCTGCAAGATGTTATGAAC   1600
 G  Y  E  M  V  F  D  G  K  P  Q  H  T  N  V  C  F  W  Y  I  P  P  S  L  R  T  L   516

GAAGACAATGAAGAGAGAATGAGTCGCCTCTCGAAGGTGGCTCCAGTGATTAAAGCCAGAATGATGGAGTATGGAACCAC   1680
 E  D  N  E  E  R  M  S  R  L  S  K  V  A  P  V  I  K  A  R  M  M  E  Y  G  T  T   543

AATGGTCAGCTACCAACCCTTGGGAGACAAGGTCAATTTCTTCCGCATGGTCATCTCAAACCCAGCGGCAACTCACCAAG   1760
  M  V  S  Y  Q  P  L  G  D  K  V  N  F  F  R  M  V  I  S  N  P  A  A  T  H  Q    569

ACATTGACTTCCTGATTGAAGAAATAGAACGCCTTGGACAAGATTTATAATAACCTTGCTCACCAAGCTGTTCCACTTCT   1840
 D  I  D  F  L  I  E  E  I  E  R  L  G  Q  D  L

CTAGGTAGACAATTAAGTTGTCACAAACTGTGTGAATGTATTTGTAGTTTGTTCCAAAGTAAATCTATTTCTATATTGTG   1920

GTGTCAAAGTAGAGTTTAAAAATTAAACAAAAAAGACATTGCTCCTTTTAAAAGTCCTTTCTTAAGTTTAGAATACCTCT   2000

CTAAGAATTCGTGACAAAAGGCTATGTTCTAATCAATAAGGAAAAGCTTAAAATTGTTATAAATACTTCCCTTACTTTTA   2080

ATATAGTGTGCAAAGCAAACTTTATTTTCACTTCAGACTAGTAGGACTGAATAGTGCCAAATTGCCCCTGAATCATAAAA   2160

GGTTCTTTGGGGTGCAGTAAAAAGGACAAAGTAAATATAAAATATATGTTGACAATAAAAACTCTTGCCTTTTTCATRAN  2240

SRNTRRTID   2249
```

*Fig. 1B*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 2249 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 53..1807

(xi) SEQUENCE DESCRIPTION: SEQ ID NO:1:

```
AGCTCGCCCG CAGCTCGCAC TCGCAGGCGA CCTGCTCCAG TCTCCAAAGC CG ATG         55
                                                         Met
                                                         1

GCA TCT CCG GGC TCT GGC TTT TGG TCT TTC GGG TCG GAA GAT GGC TCT     103
Ala Ser Pro Gly Ser Gly Phe Trp Ser Phe Gly Ser Glu Asp Gly Ser
          5                  10                  15

GGG GAT TCC GAG AAT CCC GGC ACA GCG CGA GCC TGG TGC CAA GTG GCT     151
Gly Asp Ser Glu Asn Pro Gly Thr Ala Arg Ala Trp Cys Gln Val Ala
```

```
                    20                      25                          30
CAG AAG TTC ACG GGC GGC ATC GGA AAC AAA CTG TGC GCC CTG CTC TAC         199
Gln Lys Phe Thr Gly Gly Ile Gly Asn Lys Leu Cys Ala Leu Leu Tyr
         35                      40                  45

GGA GAC GCC GAG AAG CCG GCG GAG AGC GGC GGG AGC CAA CCC CCG CGG         247
Gly Asp Ala Glu Lys Pro Ala Glu Ser Gly Gly Ser Gln Pro Pro Arg
 50              55                      60                  65

GCC GCC GCC CGG AAG GCC GCC TGC GCC TGC GAC CAG AAG CCC TGC AGC         295
Ala Ala Ala Arg Lys Ala Ala Cys Ala Cys Asp Gln Lys Pro Cys Ser
                 70                  75              80

TGC TCC AAA GTG GAT GTC AAC TAC GCG TTT CTC CAT GCA ACA GAC CTG         343
Cys Ser Lys Val Asp Val Asn Tyr Ala Phe Leu His Ala Thr Asp Leu
             85                  90              95

CTG CCG GCG TGT GAT GGA GAA AGG CCC ACT TTG GCG TTT CTG CAA GAT         391
Leu Pro Ala Cys Asp Gly Glu Arg Pro Thr Leu Ala Phe Leu Gln Asp
             100                 105                 110

GTT ATG AAC ATT TTA CTT CAG TAT GTG GTG AAA AGT TTC GAT AGA TCA         439
Val Met Asn Ile Leu Leu Gln Tyr Val Val Lys Ser Phe Asp Arg Ser
         115                     120                 125

ACC AAA GTG ATT GAT TTC CAT TAT CCT AAT GAG CTT CTC CAA GAA TAT         487
Thr Lys Val Ile Asp Phe His Tyr Pro Asn Glu Leu Leu Gln Glu Tyr
130                 135                 140                 145

AAT TGG GAA TTG GCA GAC CAA CCA CAA AAT TTG GAG GAA ATT TTG ATG         535
Asn Trp Glu Leu Ala Asp Gln Pro Gln Asn Leu Glu Glu Ile Leu Met
                 150                 155                 160

CAT TGC CAA ACA ACT CTA AAA TAT GCA ATT AAA ACA GGG CAT CCT AGA         583
His Cys Gln Thr Thr Leu Lys Tyr Ala Ile Lys Thr Gly His Pro Arg
             165                 170                 175

TAC TTC AAT CAA CTT TCT ACT GGT TTG GAT ATG GTT GGA TTA GCA GCA         631
Tyr Phe Asn Gln Leu Ser Thr Gly Leu Asp Met Val Gly Leu Ala Ala
             180                 185                 190

GAC TGG CTG ACA TCA ACA GCA AAT ACT AAC ATG TTC ACC TAT GAA ATT         679
Asp Trp Leu Thr Ser Thr Ala Asn Thr Asn Met Phe Thr Tyr Glu Ile
         195                 200                 205

GCT CCA GTA TTT GTG CTT TTG GAA TAT GTC ACA CTA AAG AAA ATG AGA         727
Ala Pro Val Phe Val Leu Leu Glu Tyr Val Thr Leu Lys Lys Met Arg
210                 215                 220                 225

GAA ATC ATT GGC TGG CCA GGG GGC TCT GGC GAT GGG ATA TTT TCT CCC         775
Glu Ile Ile Gly Trp Pro Gly Gly Ser Gly Asp Gly Ile Phe Ser Pro
                 230                 235                 240

GGT GGC GCC ATA TCT AAC ATG TAT GCC ATG ATG ATC GCA CGC TTT AAG         823
Gly Gly Ala Ile Ser Asn Met Tyr Ala Met Met Ile Ala Arg Phe Lys
             245                 250                 255

ATG TTC CCA GAA GTC AAG GAG AAA GGA ATG GCT GCT CTT CCC AGG CTC         871
Met Phe Pro Glu Val Lys Glu Lys Gly Met Ala Ala Leu Pro Arg Leu
         260                 265                 270

ATT GCC TTC ACG TCT GAA CAT AGT CAT TTT TCT CTC AAG AAG GGA GCT         919
Ile Ala Phe Thr Ser Glu His Ser His Phe Ser Leu Lys Lys Gly Ala
     275                 280                 285

GCA GCC TTA GGG ATT GGA ACA GAC AGC GTG ATT CTG ATT AAA TGT GAT         967
Ala Ala Leu Gly Ile Gly Thr Asp Ser Val Ile Leu Ile Lys Cys Asp
290                 295                 300                 305

GAG AGA GGG AAA ATG ATT CCA TCT GAT CTT GAA AGA AGG ATT CTT GAA        1015
Glu Arg Gly Lys Met Ile Pro Ser Asp Leu Glu Arg Arg Ile Leu Glu
                 310                 315                 320

GCC AAA CAG AAA GGG TTT GTT CCT TTC CTC GTG AGT GCC ACA GCT GGA        1063
Ala Lys Gln Lys Gly Phe Val Pro Phe Leu Val Ser Ala Thr Ala Gly
             325                 330                 335

ACC ACC GTG TAC GGA GCA TTT GAC CCC CTC TTA GCT GTC GCT GAC ATT        1111
Thr Thr Val Tyr Gly Ala Phe Asp Pro Leu Leu Ala Val Ala Asp Ile
```

```
                340                 345                 350
TGC AAA AAG TAT AAG ATC TGG ATG CAT GTG GAT GCA GCT TGG GGT GGG      1159
Cys Lys Lys Tyr Lys Ile Trp Met His Val Asp Ala Ala Trp Gly Gly
        355                 360                 365

GGA TTA CTG ATG TCC CGA AAA CAC AAG TGG AAA CTG AGT GGC GTG GAG      1207
Gly Leu Leu Met Ser Arg Lys His Lys Trp Lys Leu Ser Gly Val Glu
370                 375                 380                 385

AGG GCC AAC TCT GTG ACG TGG AAT CCA CAC AAG ATG ATG GGA GTC CCT      1255
Arg Ala Asn Ser Val Thr Trp Asn Pro His Lys Met Met Gly Val Pro
            390                 395                 400

TTG CAG TGC TCT GCT CTC CTG GTT AGA GAA GAG GGA TTG ATG CAG AAT      1303
Leu Gln Cys Ser Ala Leu Leu Val Arg Glu Glu Gly Leu Met Gln Asn
                405                 410                 415

TGC AAC CAA ATG CAT GCC TCC TAC CTC TTT CAG CAA GAT AAA CAT TAT      1351
Cys Asn Gln Met His Ala Ser Tyr Leu Phe Gln Gln Asp Lys His Tyr
            420                 425                 430

GAC CTG TCC TAT GAC ACT GGA GAC AAG GCC TTA CAG TGC GGA CGC CAC      1399
Asp Leu Ser Tyr Asp Thr Gly Asp Lys Ala Leu Gln Cys Gly Arg His
        435                 440                 445

GTT GAT GTT TTT AAA CTA TGG CTG ATG TGG AGG GCA AAG GGG ACT ACC      1447
Val Asp Val Phe Lys Leu Trp Leu Met Trp Arg Ala Lys Gly Thr Thr
450                 455                 460                 465

GGG TTT GAA GCG CAT GTT GAT AAA TGT TTG GAG TTG GCA GAG TAT TTA      1495
Gly Phe Glu Ala His Val Asp Lys Cys Leu Glu Leu Ala Glu Tyr Leu
                470                 475                 480

TAC AAC ATC ATA AAA AAC CGA GAA GGA TAT GAG ATG GTG TTT GAT GGG      1543
Tyr Asn Ile Ile Lys Asn Arg Glu Gly Tyr Glu Met Val Phe Asp Gly
            485                 490                 495

AAG CCT CAG CAC ACA AAT GTC TGC TTC TGG TAC ATT CCT CCA AGC TTG      1591
Lys Pro Gln His Thr Asn Val Cys Phe Trp Tyr Ile Pro Pro Ser Leu
        500                 505                 510

CGT ACT CTG GAA GAC AAT GAA GAG AGA ATG AGT CGC CTC TCG AAG GTG      1639
Arg Thr Leu Glu Asp Asn Glu Glu Arg Met Ser Arg Leu Ser Lys Val
    515                 520                 525

GCT CCA GTG ATT AAA GCC AGA ATG ATG GAG TAT GGA ACC ACA ATG GTC      1687
Ala Pro Val Ile Lys Ala Arg Met Met Glu Tyr Gly Thr Thr Met Val
530                 535                 540                 545

AGC TAC CAA CCC TTG GGA GAC AAG GTC AAT TTC TTC CGC ATG GTC ATC      1735
Ser Tyr Gln Pro Leu Gly Asp Lys Val Asn Phe Phe Arg Met Val Ile
                550                 555                 560

TCA AAC CCA GCG GCA ACT CAC CAA GAC ATT GAC TTC CTG ATT GAA GAA      1783
Ser Asn Pro Ala Ala Thr His Gln Asp Ile Asp Phe Leu Ile Glu Glu
            565                 570                 575

ATA GAA CGC CTT GGA CAA GAT TTA TAATAACCTT GCTCACCAAG CTGTTCCACT     1837
Ile Glu Arg Leu Gly Gln Asp Leu
        580                 585

TCTCTAGGTA GACAATTAAG TTGTCACAAA CTGTGTGAAT GTATTTGTAG TTTGTTCCAA    1897

AGTAAATCTA TTTCTATATT GTGGTGTCAA AGTAGAGTTT AAAAATTAAA CAAAAAAGAC    1957

ATTGCTCCTT TTAAAAGTCC TTTCTTAAGT TTAGAATACC TCTCTAAGAA TTCGTGACAA    2017

AAGGCTATGT TCTAATCAAT AAGGAAAAGC TTAAATTGT TATAAATACT TCCCTTACTT    2077

TTAATATAGT GTGCAAAGCA AACTTTATTT TCACTTCAGA CTAGTAGGAC TGAATAGTGC    2137

CAAATTGCCC CTGAATCATA AAAGGTTCTT TGGGGTGCAG TAAAAAGGAC AAAGTAAATA    2197

TAAAATATAT GTTGACAATA AAAACTCTTG CCTTTTTCAT RANSRNTRRT TD            2249

(2) INFORMATION FOR SEQ ID NO:2:

(i) SEQUENCE CHARACTERISTICS:
```

(A) LENGTH: 585 amino acids
(B) TYPE: amino acid
(D) TOPOLOGY: linear (ii) MOLECULE TYPE: protein (xi) SEQUENCE DESCRIPTION: SEQ ID NO:2:

```
Met Ala Ser Pro Gly Ser Gly Phe Trp Ser Phe Gly Ser Glu Asp Gly
 1               5                  10                  15

Ser Gly Asp Ser Glu Asn Pro Gly Thr Ala Arg Ala Trp Cys Gln Val
                20                  25                  30

Ala Gln Lys Phe Thr Gly Gly Ile Gly Asn Lys Leu Cys Ala Leu Leu
            35                  40                  45

Tyr Gly Asp Ala Glu Lys Pro Ala Glu Ser Gly Gly Ser Gln Pro Pro
        50                  55                  60

Arg Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
        355                 360                 365

Gly Gly Leu Leu Met Ser Arg Lys His Lys Trp Lys Leu Ser Gly Val
    370                 375                 380
```

-continued

```
Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
        435                 440                 445

His Val Asp Val Phe Lys Leu Trp Leu Met Trp Arg Ala Lys Gly Thr
    450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
            485                 490                 495

Gly Lys Pro Gln His Thr Asn Val Cys Phe Trp Tyr Ile Pro Pro Ser
            500                 505                 510

Leu Arg Thr Leu Glu Asp Asn Glu Glu Arg Met Ser Arg Leu Ser Lys
        515                 520                 525

Val Ala Pro Val Ile Lys Ala Arg Met Met Glu Tyr Gly Thr Thr Met
        530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
            565                 570                 575

Glu Ile Glu Arg Leu Gly Gln Asp Leu
            580                 585
```

PEPTIDE ANALOGUES OF THE 65KD ISOFORM OF HUMAN GLUTAMIC ACID DECARBOXYLASE AND USES THEREOF

TECHNICAL FIELD

The present invention relates generally to autoimmune diseases, and more specifically, to the use of peptides and peptide analogues of human glutamic acid decarboxylase in the treatment and prevention of diabetes.

BACKGROUND OF THE INVENTION

The immune system is normally prevented from mounting an attack against itself, since self is the tissue the immune system is designed to protect. To prevent such attacks, self-reactive lymphocytes are kept in check by potent regulatory mechanisms. Many, but not all, self-reactive T cells are eliminated by negative selection in the thymus. The process of negative selection is not fully understood, but T cells with too high an affinity for self peptides in the context of MHC antigens are eliminated. Paradoxically, those T cells surviving the ordeal of negative selection must then be "positively selected" or expanded. This expansion requires that the T cells be capable of recognizing self peptides in the MHC complex to a certain extent (probably lower affinity) than that seen with negative selection. This process then results in an immune system with a seemingly endless array of specificities.

In North America, five percent of adults, more than two-thirds of them women, suffer from autoimmune diseases (including: multiple sclerosis, rheumatoid arthritis, juvenile diabetes, systemic lupus erythematosus, and thyroiditis). Self-reactive T cells that escape thymic selection are found in all healthy individuals. Therefore, regulation of self reactivity is also maintained, in part, through mechanisms acting outside the thymus. These mechanisms include: active suppression by other cells (i.e., suppressor T cells) that keep these autoreactive lymphocytes under control and by clonal unresponsiveness (anergy), where the cells reactive to self are "anergized." Anergy is thought to involve the inappropriate presentation of the antigenic peptide to the T cell, which leads to unresponsiveness or tolerance. Peptide affinity may play a role in whether the T cell is turned on or off. If the immune system does react against self tissue, a harmful if not potentially fatal autoimmunity develops. One popular theory for autoimmunity is that those people who are genetically predisposed to autoimmune diseases come in contact with infectious agents, such as viruses or bacteria. In the process of controlling the infection, the immune system targets an antigen on the pathogen that resembles a self antigen. These cells then begin to attack self tissue, resulting in autoimmunity.

Insulin-dependent diabetes (IDDM) is one of the most serious and common metabolic disorders. IDDM was once viewed as a rapidly developing illness similar to that which might occur as the result of an acute viral infection, but in fact it results from a chronic autoimmune process that usually exists for years in a preclinical phase. Indeed, the classic manifestations of IDDM—hyperglycemia and ketosis—occur late in the course of the disease after most of the beta cells have been destroyed.

The most striking histological feature of the pancreas of a patient with long-standing IDDM is the near total lack of insulin-secreting beta cells. By contrast, islet cells secreting glucagon (alpha cells), somatostatin (delta cells), or pancreatic polypeptide (pancreatic-polypeptide cells) are preserved. Since beta cells constitute the majority (70 percent) of cells within normal islets, the islets of a patient with long-standing diabetes are abnormally small. Aside from mild interstitial fibrosis and exocrine atrophy, there are no other obvious histologic abnormalities.

At the time of the onset of IDDM or shortly thereafter, most islets are deficient in beta cells, just like the islets in patients with long-standing disease. The remaining islets contain cells with enlarged nuclei, variable numbers of degranulated beta cells, and a chronic inflammatory infiltrate commonly referred to as insulitis. This inflammatory infiltrate consists mostly of CD8 cells plus variable numbers of CD4 cells, B lymphocytes, macrophages, and natural killer cells. The expression of HLA class I molecules on islet cells is increased, whereas class II molecules may be overexpressed on beta cells, macrophages, or endothelium. The expression of intercellular adhesion molecule 1 on the vascular endothelium of the islets is also increased, a feature favoring the adhesion and accumulation of endothelial cells.

The distribution of islets with insulitis in the pancreas of patients with newly diagnosed IDDM can be strikingly uneven. The islets in one pancreatic lobule may appear normal, while those in adjacent lobules may be small or have profound insulitis. This variability may reflect the different insulin-secreting activities of the islet cells, with the most metabolically active beta cells being preferentially destroyed. Histologic studies suggest that an 80 percent reduction in the volume of beta cells is required to induce symptomatic IDDM. Histologic evidence of islet regeneration is uncommon, but it is found in the pancreas of some young patients with IDDM.

The diabetes results from the autoimmune destruction of the insulin-producing β cells of the pancreas and the subsequent metabolic derangements. Although insulin therapy allows most patients to lead active lives, this replacement is imperfect since it does not restore normal metabolic homeostasis. Metabolic abnormalities are thought to be important in the subsequent development of common complications, which include retinopathy, cataract formation, nephropathy, and heart disease.

While the initiating agent of IDDM autoimmunity is not known, it ultimately provokes a loss of immunological tolerance to self-antigens present in insulin-secreting B cells within the pancreatic islets. IDDM begins with an asymptomatic stage, characterized by a chronic inflammatory infiltrate of the islets mediated by white blood cells, including T lymphocytes, B lymphocytes and macrophages which selectively destroys the beta islet cells.

Autoimmunity to beta cells can be initiated by one of two processes. An immune response against a viral protein that shares an amino acid sequence with a beta-cell protein could result in the appearance of antiviral cytotoxic CD8 lymphocytes that react with self-protein on the beta cells. Alternatively, an environmental insult (infection with a beta-cell-tropic virus or expression of a beta-cell superantigen) may generate cytokines and other inflammatory mediators that induce the expression of adhesion molecules in the vascular endothelium of the pancreatic islets. The activation of endothelial cells would allow increased adhesion and extravasation of circulating leukocytes and the presentation of beta-cell antigens from the damaged beta cells by infiltrating macrophages to lymphocytes.

With either alternative, the autoimmune process would be enhanced as soon as lymphocytes reacting with antigens released from damaged beta cells were recruited to the site of inflammation. Genetic susceptibility to IDDM includes an inherent defect in the establishment of peripheral tolerance to beta-cell autoantigens. The continued release of inflammatory cytokines from the inflamed islets could result in the overexpression of HLA class I molecules on beta cells, further potentiating their destruction. As the autoimmune process proceeds, various effector mechanisms of immunologic destruction result in the elimination of beta cells.

The steps in T cell activation in autoimmune diseases are no different than in normal immune regulation. The first step in activation (signal 1) requires interaction among the components of the ternary complex: the T cell receptor, MHC gene products, and the nominal peptide antigen. The second step (signal 2) is not yet clear, but may involve either cytokines or accessory molecules on the antigen presenting cells' surface (such as CD28 ligand). If the T cell receives only signal 1 unresponsiveness or anergy results. Knowing how T cells responds to antigens could allow modulation of the response so that the immune system would respond better to the peptide. Conversely, altering the recognition of a self-peptide could be a useful therapy in managing autoimmune diseases.

SUMMARY OF THE INVENTION

The present invention provides peptides and peptide analogues of the 65 kD isoform of human glutamic acid decarboxylase for use in the treatment and prevention of diabetes. More specifically, within one aspect, the peptide consists from seven to fifteen amino acids selected from residues 521–535 of the 65 kD isoform of human GAD.

Within a related aspect, peptide analogues are provided comprising at least seven amino acids selected from residues 521–535 of the 65 kD isoform of human GAD, wherein at least one amino acid from those residues corresponding to 521–535 is altered to an amino acid other than the amino acid present in the native protein at that position. Within certain embodiments, the amino acid is altered to an amino acid selected from the groups consisting of arginine, asparagine, histidine, leucine, serine, glycine, glutamic acid, phenylalanine and alanine. Within a related embodiment, the N-terminal amino acid or both the N-terminal and C-terminal amino acids of the peptide analogue are D-amino acids.

Within another related aspect, peptide analogues are provided comprising at least seven amino acids selected from residues 521–535 of the 65 kD isoform of human GAD, wherein one to three L-amino acids selected from the group consisting of arginine at position 525, lysine at position 528, proline at position 531 and lysine at position 534 are altered to an amino acid other than the amino acid present in the native protein at that position.

Within other aspects of the subject invention, a series of peptide analogues comprising at least seven amino acids selected from residues (a) 173–187, (b) 177–191, (c) 193–207, (d) 201–215, (e) 213–227, (f) 493–507, (g) 505–519, (h) 525–539, (i) 533–547 and (j) 537–551 of the 65 kD isoform of human GAD are provided, wherein at least one amino acid from those residues corresponding to the above-identified portions is altered to an amino acid other than the amino acid present in the native protein at that position.

It will also be understood by those skilled in the art that several amino acids within the peptide analogue may be altered, although generally anywhere from one to five alterations are preferred. In this regard, it is also generally preferred to maintain residues corresponding to MHC contact sites. For instance, within a peptide analogue comprising amino acids selected from residues 521–535 of the 65 kD isoform of human GAD, it is generally preferred to maintain the amino acid residues corresponding to positions 523, 526, 529, 532 and 533.

Further aspects of the present invention provide pharmaceutical compositions comprising a peptide analogue as described herein in combination with a physiologically acceptable carrier or diluent. In addition, within a related aspect, methods of treating diabetes have provided, comprising administering to a patient a therapeutically effective amount of such a pharmaceutical composition.

In still other aspects of the present invention, methods of detecting diabetes are provided, comprising: (a) contacting a portion of a biological sample from a patient with a first peptide or peptide analogue as described herein; (b) contacting a separate portion of the biological sample with a second peptide comprising from seven to fifteen amino acids selected from residues 161–175 of the 65 kD isoform of human GAD; and (c) detecting the response to the first and second peptides, and therefrom determining whether the patient has diabetes. Within a related aspect, a method for detecting a predisposition to diabetes is provided, comprising: (a) contacting a biological sample from an individual at risk of developing diabetes with a peptide comprising from seven to fifteen amino acids selected from residues 161–175 of the 65 kD isoform of human GAD; (b) detecting the response to the peptide from step (a); (c) contacting a second biological sample from the individual with a peptide comprising from seven to fifteen amino acids selected from residues 161–175 of the 65 kD isoform of human GAD at a time sufficiently subsequent to performing step (a) to allow a maturation of the immune response; (d) detecting the response to the peptide from step (c); and (e) comparing the values obtained from steps (b) and (d), and therefrom determining a predisposition to diabetes.

These and other aspects of the invention will become evident upon reference to the following detailed description and attached drawings. In addition, various references are set forth below which describe in more detail certain procedures or compositions. Each of these references are incorporated herein by reference in their entirety as if each were individually noted for incorporation.

BRIEF DESCRIPTION OF THE DRAWINGS

FIGS. 1A and 1B depict DNA and predicted amino acid sequence (SEQ ID NOS. 1 and 2) for the 65 kD isoform of human glutamic acid decarboxylase.

DETAILED DESCRIPTION OF THE INVENTION

Figure 2:
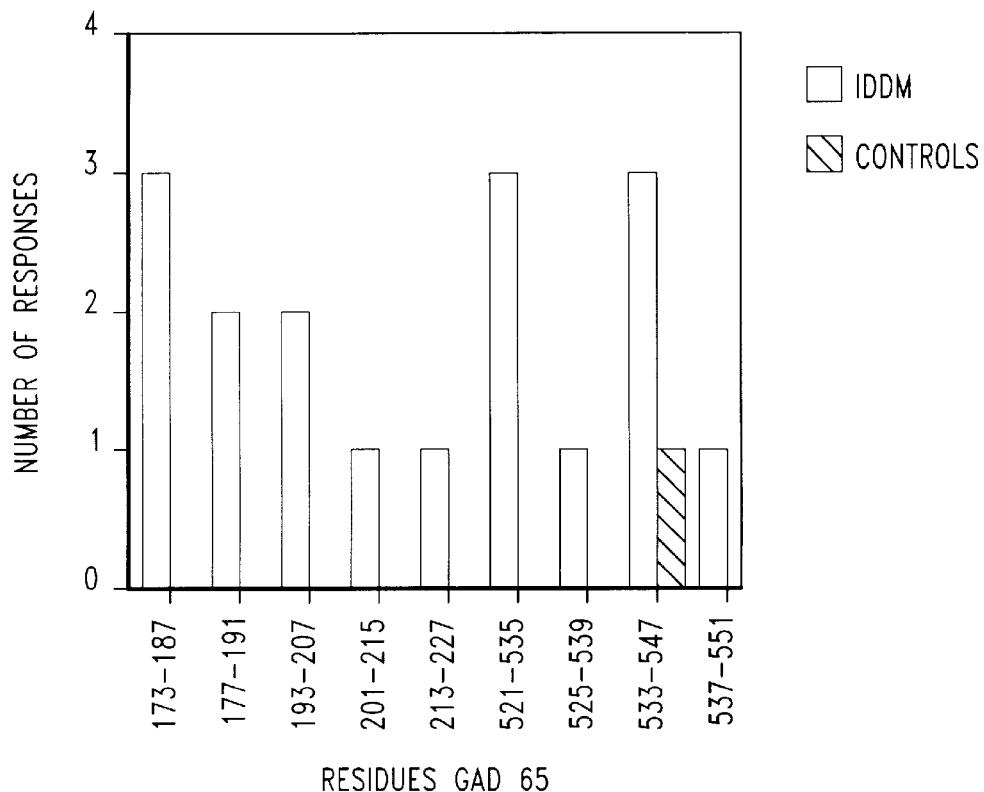
FIG. 2 is a graph illustrating the T cell proliferative responses to peptides corresponding to various regions of GAD 65. Responses to peptides (5 μg/ml) in 5–7 Type 1 diabetic patients (solid bars) and 4–5 healthy controls (hatched bars) are expressed by the number of responders (y-axis). Background counts were normally between 600 and 3000 cpm, while positive wells had to exceed 1500 and 6000 cpm respective to background counts.

Prior to setting forth the invention, it may be helpful to an understanding thereof to set forth definitions of certain terms that will be used hereinafter.

Glutamic acid decarboxylase ("GAD") refers to an enzyme expressed in β cells of the pancreas and in neurons of the central nervous system. There are two isoforms of GAD, "GAD 65" and "GAD 67." "GAD 65" is also referred to herein as the "65 kD isoform of human glutamic acid decarboxylase." The nucleotide sequence and predicted amino acid sequence of human GAD 65 are presented in FIG. 1 (SEQ ID NOS. 1 and 2). Although not depicted in FIG. 1, different molecular forms of human glutamic acid decarboxylase generated by differential splicing or post-translational modification are also within the scope of this invention.

"Peptide analogues" of GAD are at least seven amino acids in length and contain at least one difference in amino acid sequence between the analogue and native human GAD. Unless otherwise indicated, a named amino acid refers to the L-form. An L-amino acid from the native peptide may be altered to any other one of the 20 L-amino acids commonly found in proteins, any one of the corresponding D-amino acids, rare amino acids, such as 4-hydroxyproline, and hydroxylysine, or a non-protein amino acid, such as β-alanine and homoserine. Also included with the scope of the present invention are amino acids which have been altered by chemical means such as methylation (e.g., α-methylvaline), amidation of the C-terminal amino acid by an alkylamine such as ethylamine, ethanolamine, and ethylene diamine, and acylation or methylation of an amino acid side chain function (e.g., acylation of the epsilon amino group of lysine).

"Residue 522," "residue 525," "residue 528, " "residue 531" and "residue 534" (also called position 522, position 525, position 528, position 531 and position 534, respectively), refer to amino acids 522, 525, 528, 531 and 534 of human glutamic acid decarboxylase as depicted in FIG. 1 or the amino acid at a comparative position. More specifically, the numbering system for these residues relates to the amino acid position within the native human protein, regardless of the length of the peptide or the amino acid position within that peptide.

Figure 4:
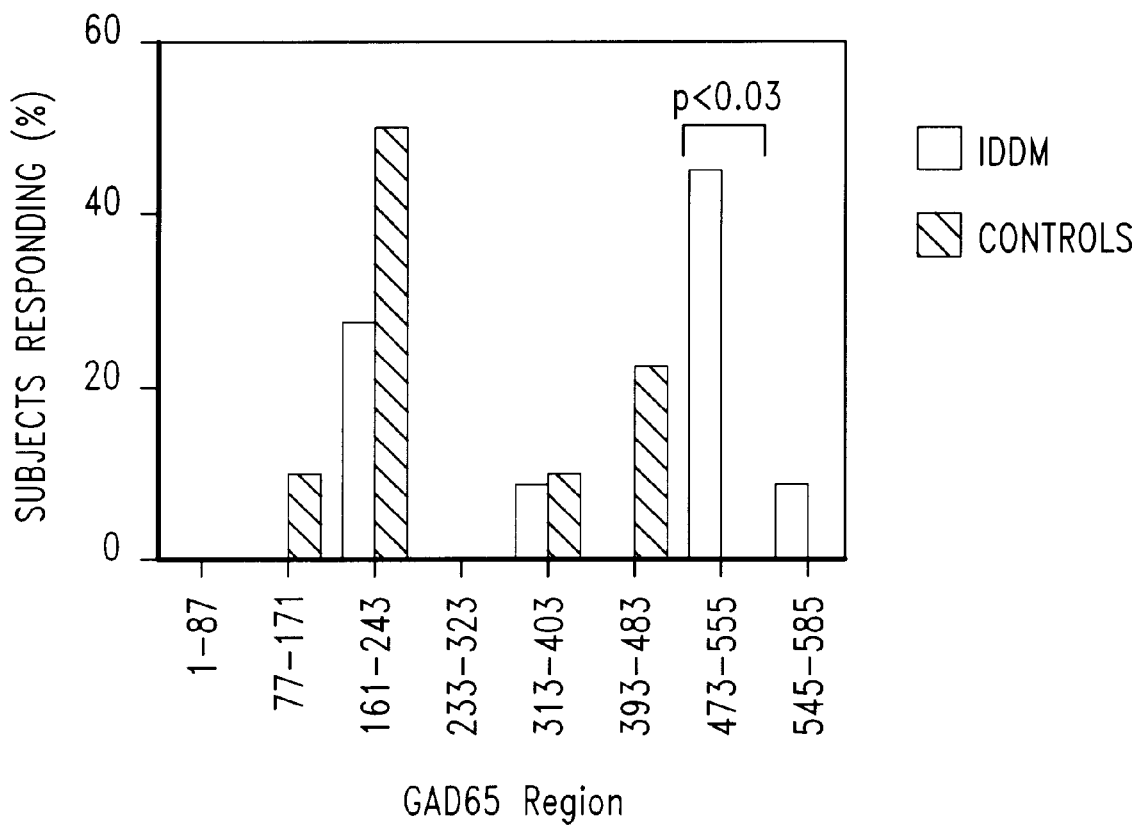
FIG. 4 is a graph illustrating the proliferative response of human T cells from IDDM patients or normal controls to various regions of GAD 65. Results are expressed as percentage of subjects responding to immunodominant regions defined by residue numbers. Significant differences between patients and controls were observed for region 473–555.

A major focus of research into autoimmunity is the identification of dominant epitopes on disease-associated auto-antigens recognized by autoreactive T cells. Immunodominant regions of the antigen GAD 65 have been identified in Type 1 diabetic patients (Lohmann et al., *Lancet* 343:1607–08, 1994; Atkinson et al., *J Clin. Invest.* 94:2125–2129, 1994). Within the subject invention, a detailed T cell epitope mapping of immunodominant regions in patients with Type 1 diabetes was performed. Two regions of GAD 65 were selected for decoding, representing the regions associated with the highest frequency of T cell responses in both Type 1 diabetics (amino acid residues 473–555 and 161–243) and control subjects (amino acid residues 161–243) (FIGS. 2 and 4). Nine diabetics who responded to region 473–555 were selected for further study of their response to 18 single peptides covering this region. T cell reactivity was found to only 7 peptides. Nearly half the patients tested, but none of the controls, responded to peptide 521–535 (FIG. 2). It is likely that T cell reactivity to peptide 521–535 of GAD 65 is not genetically determined, because the non-diabetic identical co-twins of two Type 1 diabetics who responded to this peptide did not respond themselves. Other regions which exhibited T cell reactivity predominantly in diabetic patients included 525–539, 533–547 and 537–551 (FIG. 2). Peptide mapping data were confirmed by establishing T cell clones specific for selected peptides in responsive individuals, for example to peptides 521–535 and 505–519.

Type 1 diabetes is associated with the HLA DQβ1*0302 allele (Nepom and Erlich, *Ann. Rev. Immunol.* 9:493–525, 1991). Transgenic NOD mice expressing the human DQβ1*0302 gene were constructed. T cells from these mice are stimulated to proliferate by peptides 493–507 and 505–519, as well as by GAD 65 native protein. Thus, these peptides are recognized by T cells in the context of DQβ1*0302 and are additional peptides suitable for use in the present invention.

Another region of interest, peptide 161–243, was immunodominant in a similar proportion of both Type 1 diabetics and controls. Region 161–243 was decoded in order to define whether the same epitopes within this region are recognized by diabetics and controls. Epitope mapping of this region indicated that none of the peptides used to decode it was recognized by both patients and controls. Peptides 173–187, 177–191, 193–207, 201–215 and 213–227 were only recognized by Type 1 diabetic patients (FIG. 2). However, T cell responses to peptide 173–187 were not simply associated with having diabetes, since T-cells from non-diabetic identical co-twins of two diabetics who were peptide responders also responded to this peptide. If genetic factors exclusively determined reactivity to peptide 173–187, then identical twins, whether diabetic or non-diabetic, should show a similar peptide reactivity. Twins studied showed similar responsiveness to peptides 173–187 and 177–191, which is consistent with a strict genetic effect.

Environmental factors can modulate profiles of epitope recognition. For instance, after immunization there is spreading of epitope recognition both to other molecules and within a particular molecule (Lohmann et al., *Immunol. Today* 14:203–206, 1993). Furthermore, studies of transgenic animals has demonstrated the existence of a subdominant T cell repertoire which is modulated by the amount of available antigen (Cabaniols et al., *Eur. J Immunol.* 24:1743–1749, 1994). These subdominant or cryptic (i.e., not normally available for recognition) epitopes may be important in the development of autoimmunity (Sercarz et al., *Ann. Rev. Immunol. 11:729–766*). Environmental factors can modulate profiles of epitope recognition. For example, peptide 161–175 was recognized by two control subjects, but by none of the diabetic patients. T cells from diabetic identical twins also failed to recognize this peptide, although their non-diabetic co-twins did respond to it. Therefore, reactivity to some peptides, such as 521–535, is specifically associated with disease, whereas, other peptides, such as 161–175, are only recognized by subjects without Type 1 diabetes. Thus, the differential reactivity between Type 1 diabetics and controls can be used within a method for detecting a predisposition to diabetes.

The peptides described herein can be utilized to develop analogues that specifically interact with and functionally inactivate pathogenic T cells from IDDM patients or individuals predisposed to develop IDDM. Normally, peptides are recognized by the immune system through binding to the MHC by key anchor or contact residues, while other amino acids within the peptide are essential for recognition by T cells (T cell contact sites). As described herein, alteration of native peptides with selective changes of crucial residues (altered peptide ligands or "APL") can induce unresponsiveness or change the responsiveness of antigen-specific autoreactive T cells. The mechanism of action of how altered peptide ligands may involve incomplete mobilization of the T cell receptor (TCR). There are several possible functional alterations that the APL can induce and these include:

(a) Simple antagonist—the APL may just compete for MHC binding with the native peptide on the antigen presenting cell and not allow for complete T cell activation. This implies that there is no signal transmitted through the T cell receptor by the APL.

(b) Anergy—the APL induces a state of complete nonresponsiveness as in the T cell such that the T cell does not respond to the native peptide.

(c) Phenotypic switching—the APL may induce a functional switch in the T cell such that it decreases the production of proinflammatory cytokines and/or increase the production of noninflammatory cytokines such as IL-4 or IL-10.

Peptide Analogues of Glutamic Acid Decarboxylase

As noted above, the present invention provides peptide analogues comprising at least seven amino acids, for instance selected from residues 521–535 of human GAD and including an alteration of a naturally occurring amino acid to another amino acid. The peptide analogues are preferably 7 to 20 amino acids, and usually not longer than 25 amino acids. Particularly preferred peptide analogues are 15 amino acids in length. Any amino acid alteration is within the scope of this invention. Preferred peptide analogues include alteration of the L-amino acid to any one of the following amino acids: D-lysine, alanine, glycine, glutamic acid, phenylalanine, arginine, asparagine, histidine, leucine or serine. These amino acids include both conservative (similar charge, polarity, hydrophobicity, and bulkiness) and non-conservative amino acids. Although typically one might expect that only non-conservative amino acid alterations would provide a therapeutic effect, unexpectedly even conservative changes (e.g., arginine) greatly affect the function of the peptide analogue as compared to the native peptide. Such diversity of substitution is further illustrated by the fact that the preferred amino acids noted above are hydrophobic and hydrophilic, charged and uncharged, polar and nonpolar.

Peptides and peptide analogues may be synthesized by standard chemistry techniques, including synthesis by automated procedure. In general, peptide analogues are prepared by solid-phase peptide synthesis methodology which involves coupling each protected amino acid residue to a resin support, preferably a 4-methylbenzhydrylamine resin, by activation with dicyclohexylcarbodiimide to yield a peptide with a C-terminal amide. Alternatively, a chloromethyl resin (Merrifield resin) may be used to yield a peptide with a free carboxylic acid at the C-terminus. Side-chain functional groups are protected, for example, as follows: benzyl for serine, threonine, glutamic acid, and aspartic acid; tosyl for histidine and arginine; 2-chlorobenzyloxycarbonyl for lysine and 2,6-dichlorobenzyl for tyrosine. Following coupling, the t-butyloxycarbonyl protecting group on the alpha amino function of the added amino acid is removed by treatment with trifluoroacetic acid followed by neutralization with di-isopropyl-ethylamine. The next protected residue is then coupled onto the free amino group, propagating the peptide chain. After the last residue has been attached, the protected peptide-resin is treated with hydrogen fluoride to cleave the peptide from the resin, as well as deprotect the side chain functional groups. Crude product can be further purified by gel filtration, HPLC, partition chromatography, or ion-exchange chromatography.

Peptide analogues within the present invention should (a) compete for binding with the corresponding native GAD peptide to MHC; and (b) not cause proliferation of the corresponding native peptide-specific T cells.

Thus, candidate peptide analogues may be screened for their ability to treat diabetes by (1) an assay measuring competitive binding to MHC, and (2) an assay measuring T cell proliferation. Those analogues that inhibit binding of the native peptides and do not stimulate proliferation of GAD-reactive T cells are useful therapeutics.

Binding of peptides to MHC molecules may be assayed on whole cells. Briefly, human peripheral blood transformed with Epstein-Barr Virus (EBV) expressing the appropriate Class II molecules are employed in the assay. The binding of peptide analogues to cells is measured by a fluorescence assay. In this assay, EBV-transformed B cells are mixed with different concentrations of peptide analogues and incubated for 1 hour at 37° in a $CO_2$ incubator. Following incubation, the corresponding native GAD peptide is biotin-labeled and added to the culture wells. The cells are incubated for another hour and then washed three times in medium. Phycoerythrin-conjugated or fluorescein-conjugated streptavidin is added and the cells incubated for approximately 30 minutes on ice. Following incubation, the cells are washed twice before analysis by flow cytometry. Fluorescence intensity is calculated by subtracting the fluorescence value obtained from cells stained with phycoerythrin-streptavidin alone (control staining) from the fluorescence value obtained from biotin-labeled GAD pepride plus phycoerythrin-streptavidin (experimental staining). Staining without analogue establishes a 100% value. Percent inhibition is calculated for each analogue and expressed as $IC_{50}$ values. A peptide analogue with an $IC_{50}$ value of less than 100 μM is suitable for further screenings.

Candidate peptide analogues are further tested for their property of stimulating or inhibiting proliferation of T cells. Two different assays may be used as alternatives. The first measures the ability of the analogue to cause proliferation of T cells in a direct fashion. The second assay measures the ability of the peptide analogue to inhibit proliferation of T cells induced by native GAD peptide.

In the direct proliferation assay, the corresponding native GAD peptide reactive T cells are used as target cells. T cell clones were tested in triplicate for proliferation over 3 days in triplicate in round-bottomed microtiter wells. Ten thousand T cells of each clone were washed once and added to 2–3×10⁴ irradiated (4500 rads) autologous PBMCs or irradiated (16,000 rads) Epstein-Barr Virus (EBV) transformed B cells together with 10 μg/ml of the appropriate peptide. 0.5 μCi [³H]-thymidine was added during the final 6 hours before harvesting and counting. The stimulation index (SI) was calculated as (total cpm with T cells, APCs and antigen/cpm with T cells and APCs alone).

The second or alternative assay is a competition assay for T cell proliferation. In this assay, antigen presenting cells (e.g., EBV-transformed B cells) are first irradiated and then incubated with the corresponding native GAD peptide for 2–4 hours. These cells are then washed and further cultured with T cells reactive to the GAD peptide. Various concentrations of candidate peptide analogues are included in cultures for an additional 3 days. Following this incubation period, each culture is pulsed with 1 μCi of [³H]-thymidine for an additional 12–18 hours. Cultures are then harvested on fiberglass filters and counted as above. Mean CPM and standard error of the mean are calculated from data determined in triplicate cultures. Peptide analogues which inhibit proliferation to approximately 25% at a concentration of 50 μM or greater are suitable for further screening.

Candidate peptides that compete for binding of GAD to MHC and do not cause direct proliferation of T cells and/or can inhibit proliferation by the corresponding native GAD peptide, may be used as described herein.

Treatment of Diabetes

As noted above, the present invention provides methods for treating diabetes by administering to the patient a therapeutically effective amount of a peptide analogue of human GAD as described herein. Patients suitable for such treatment may be identified by criteria establishing a diagnosis of IDDM as defined by the National Diabetes Data Group (Gleichman et al., *Diabetes* 38:578–584, 1987).

Effective treatment of diabetes may be examined in several different ways. Satisfying any of the following criteria evidences effective treatment. The main criteria used are (a) reduction in the need for exogenous insulin, (b) increased production of endogenous insulin, and (c) normalization of plasma glucose levels.

Individuals at risk of developing IDDM, and therefore candidates for fie preventative treatment described herein, are individuals whose genotype is positively correlated with diabetes (e.g., HLA-DR1, DR3, DR4, DQ1, DQ2, DQ6 and DQ8) and relatives of IDDM patients. These individuals can also be identified by the presence of auto-reactive antibodies to various autoantigens, such as insulin, islet cell antigen and GAD.

Efficacy of the peptide analogue in the context of prevention is judged based on the following criteria: frequency of GAD reactive T cells determined by limiting dilution, proliferation response of GAD reactive T cell lines and clones, cytokine profiles of T cell lines and clones to GAD established from patients. Efficacy is established by decrease in frequency of reactive cells, a reduction in thymidine incorporation with altered peptide compared to native, and a reduction in TNF and IFN-γ.

Peptide analogues of the present invention may be administered either alone, or as a pharmaceutical composition. Briefly, pharmaceutical compositions of the present invention may comprise one or more of the peptide analogues described herein, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol, proteins, polypeptides or amino acids such as glycine, antioxidants, chelating agents such as EDTA or glutathione, adjuvants (e.g., aluminum hydroxide) and preservatives. In addition, pharmaceutical compositions of the present invention may also contain one or more additional active ingredients, such as, for example, immunosuppressive agents.

Compositions of the present invention may be formulated for the manner of administration indicated, including for example, for oral, nasal, venous, intracranial, intraperitoneal, subcutaneous, or intramuscular administration. Within other embodiments of the invention, the compositions described herein may be administered as part of a sustained release implant. Within yet other embodiments, compositions of the present invention may be formulized as a lyophilizate, utilizing appropriate excipients which provide stability as a lyophilizate, and subsequent to rehydration.

Pharmaceutical compositions of the present invention may be administered in a manner appropriate to the disease to be treated (or prevented). The quantity and frequency of administration will be determined by such factors as the condition of the patient, and the type and severity of the patient's disease. Within particularly preferred embodiments of the invention, the peptide analogue or pharmaceutical compositions described herein may be administered at a dosage ranging from 5 to 50 mg/kg, although appropriate dosages may be determined by clinical trials. Patients may be monitored for therapeutic effectiveness by monitoring blood glucose levels and/or reduction in the level of autoantibodies to glutamic acid decarboxylase.

The following examples are offered by way of illustration and not by way of limitation.

EXAMPLES

EXAMPLE 1

Production of GAD 65 Peptides

A series of 15 mers overlapping by 11 residues completely covering GAD 65 were synthesized by the multipin method (Reece et al., *J Immunol.* 151:6175–6184, 1993). Peptides were cleaved in 0.05 M HEPES pH 7.5–7.6 in 40% acetonitrile (HPLC grade)water and the purity of representative peptides was assessed using IPLC as >80%.

EXAMPLE 2

Preparation of GAD peptide analogues

The peptides were synthesized by solid phase methodology on a peptide synthesizer (Beckman model 990). Peptides with an amidated carboxyl-termiinus were prepared with a p-methylbenzhydrylamine resin (MBHA resin); for peptides with a free carboxyl-terminus, a Merrifield resin coupled with the appropriately protected amino acid was used. Both resins were obtained from Bachem Fine Chemicals (Torrance, Calif.). Derivatized amino acids (Bachem Fine Chemicals) used in the synthesis were of the L-configuration unless specified otherwise, and the N-alpha-amino function protected exclusively with the t-butyloxycarbonyl group. Side-chain functional groups were protected. For example: benzyl for serine, threonine, glutamic acid, and aspartic acid; tosyl for histidine and arginine; 2-chlorobenzyloxycarbonyl for lysine and 2,6-dichlorobenzyl for tyrosine. Coupling of the carboxyl-terminal amino acid to the MBHA resin was carried out with dicyclohexylcarbodiimide and the subsequent amino acids were coupled with dicyclohexylcarbodiimide according to Ling et al. (*Proc. Natl. Acad. Sci. USA* 81:4302, 1984). After the last amino acid was incorporated, the t-butyoxycarbonyl protecting group was removed and the peptide-resin conjugate treated with a mixture of 14 ml hydrofluoric acid (HF), 1.4 ml anisole, and 0.28 ml methylethyl sulfide per gram of resin conjugate at −20° C. for 0.5 hr and at 0° C. for 0.5 hr. HF was removed in vacuum at 0° C., and the resulting peptide and resin mixture was washed twice with diethyl ether and twice with chloroform and diethyl ether alternately. The peptide was extracted five times with 2 M acetic acid, and the extract lyophilized. The lyophilized product was first purified on a column of Sephadex G-25 fine (Pharmacia-LKB, Piscataway, N.J.) developed in 30% acetic acid to remove the truncated fragments and inorganic salts (Ling et al., 1984). Next, peptides were further purified by CM-32 carboxymethylcellulose cation-exchange chromatography (Ling et al., 1984). Final purification was achieved by partition chromatography on Sephadex G-25 fine (Ling et al., 1984). The synthetic product was characterized by amino acid analysis, mass spectrometric analysis, and reversed-phase HPLC.

EXAMPLE 3
Long-term human T cell lines

Figure 3:
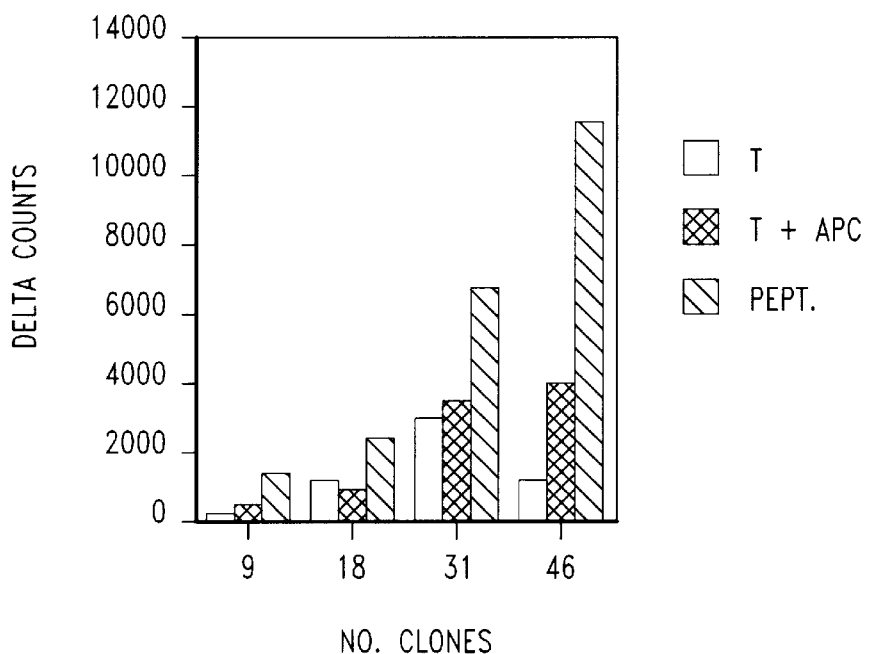
FIG. 3 is a graph illustrating the proliferative response of T cell clones from an IDDM patient to GAD 521–535. Four clones from a Type 1 diabetic patient responded to peptide 521–535 of GAD 65 (10 μg/ml). All clones showed responses with a stimulation index greater than 2; the counts exceeded 1000 cpm and the standard deviation of triplicate samples were <15%. Conditions include: T cells alone (solid bars), T cells with antigen presenting cells (stippled bar), or T cells with antigen presenting cells and GAD 521–535.

Establishment of GAD peptide-specific T cell clones. Peptide-specific clones were generated from a healthy individual, PS (control A1 in Table 1), and 2 Type 1 diabetics, SK and ST (Type 1 patients B1 and B6 in Table 1). PBMC ($5\times10^6$) were stimulated for 4–5 days with peptide. PMBC were further cultured for 5 days (RPMI 1640/10% human serum) in the presence of interleukin 2 (IL-2, 20 ng/ml). Cells were then plated at 0.3 cells/well in a 96 well plate (Nunc) and stimulated by irradiated (4500 rads=45 Gy), heterologous peripheral blood mononuclear cells (PBMCs, $1\times10^6$ cells/ml), 35 ng/ml anti-CD3 monoclonal antibody (OKT3, ATCC, Maryland), and 20 ng/ml IL-2 (Hoffmann-La Roche, Nutley, N.J.). Further expansion and maintenance of all clones was achieved by restimulation every 1–2 weeks with OKT3, IL-2 and irradiated, heterologous PBMCs. Assays were performed at the end of the cycle and a minimum of 5 days after the last exposure to IL2. Clones were tested in triplicate in proliferation assays performed in round-bottomed microtitration wells (FIG. 3). T cells ($1\times10^3$) of each clone were washed once and added to $2-3\times10^4$ irradiated (4500 rads) autologous PBMCs or irradiated (16,000 rads) Epstein-Barr Virus (EBV) transformed B cells (see below) together with 10 μg/ml of the appropriate peptide. 0.5 μCi [$^3$H]-thymidine was added during the final 6 hours before harvesting and counting. The stimulation index (SI) was calculated as (total cpm with T cells, APCs (antigen presenting cells) and antigen/cpm with T cells and APCs alone). All four clones tested responded to peptide 521–535 of GAD 65 (FIG. 3).

EXAMPLE 4
Antigen-specific human T cell line proliferation assays

Proliferation assays. Proliferation assays were performed in 96 well round bottomed plates (Nunc, Roskilde, Denmark) with $2\times10^5$ cells per well in a final volume of 20 μl/well. Tetanus toxoid (TT), phytohemagglutinin (PHA, Difco, East Molesey, UK) and a set of immunodominant tetanus toxoid peptides (Reece et al., *J Immunol.* 115:6175–6184, 1993) were used as positive controls. 16 wells for each peptide pool (GAD- or TT-peptides), 32 negative control wells and 8 wells for both positive controls (PHA and TT) were used. Alternatively, in 7 day assays, 12 wells per peptide, 24 negative control wells and 3 wells per positive control were plated. Cultures were incubated at 37° C., 5% $CO_2$ atmosphere for 4 or 7 days. During the last 6 hours, 0.5 μCi of [$^3$]-thymidine (Amersham, Little Chalfont, UK) per well was added before harvesting and scintillation counting using a betaplate counter (Wallac, Turku, Finland).

Our studies revealed that there was a difference in which regions of the molecule were recognized by IDDM T cells compared to normals. While the immunodominant region of GAD recognized by T cells from both normals and IDDM patients was directed towards the center of the molecule (e.g., residues 161–243), region 473–555 was only recognized by T cells from IDDM patients. As seen in FIG. 2, Type 1 diabetic patients responded exclusively to peptides 173–187 (3/7), 177–191 (2/7), 193–207 (2/7), 201–215 (1/7), 213–227 (1/7), 521–535 (3/7), 525–539 (1/7), and 537–551 (1/7). Another peptide, 533–547, stimulated 3 out of 7 T cells from diabetics compared with one of the controls. In addition, 2 non-diabetic co-twins were unresponsive to peptide 521–535, although their diabetic twins did respond to this peptide. Moreover, as shown earlier, responses to the 161–175 region were exclusively seen in the non-diabetic (data not shown). T cell clones specific to GAD 521–535 were established from an IDDM patient and their response to the peptide shown in FIG. 3.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A peptide analogue of 7 to 25 amino acids comprising at least seven contiguous amino acids selected from residues corresponding to 521–535 of SEQ. ID. NO: 2, wherein one to five amino acids from those residues corresponding to 521–535 is altered to an amino acid other than the amino acid present in the native protein at that position, and wherein the peptide analogue competes for binding with the native glutamic acid decarboxylase (GAD) peptide to MHC and does not stimulate proliferation of GAD-reactive T-cells.

2. The peptide analogue of claim 1 wherein the N-terminal amino acid of the peptide analogue is a D-amino acid.

3. The peptide analogue of claim 1 wherein one amino acid is altered, and wherein the amino acid which is to be altered is selected from the group consisting of arginine at position 522, arginine at position 525, lysine at position 528, proline at position 531 and lysine at position 534.

4. The peptide analogue of claim 1 wherein the arginine residue at position 522 is altered to another amino acid.

5. The peptide analogue of claim 4 wherein the arginine residue at position 522 is altered to an alanine residue.

6. The peptide analogue of claim 1 wherein the arginine residue at position 525 is altered to another amino acid.

7. The peptide analogue of claim 6 wherein the arginine residue at position 525 is altered to an alanine residue.

8. The peptide analogue of claim 1 wherein the lysine residue at position 528 is altered to another amino acid.

9. The peptide analogue of claim 8 wherein the lysine residue at position 528 is altered to an alanine residue.

10. The peptide analogue of claim 1 wherein the proline residue at position 531 is altered to another amino acid.

11. The peptide analogue of claim 10 wherein the proline residue at position 531 is altered to an alanine residue.

12. The peptide analogue of claim 1 wherein the lysine residue at position 534 is altered to another amino acid.

13. The peptide analogue of claim 12 wherein the lysine residue at position 534 is altered to an alanine residue.

14. The peptide analogue of claim 1 wherein each of the altered amino acids is altered to an amino acid other than the amino acid present in the native protein at that position, each of said altered amino acids being altered to an amino acid selected from the group consisting of arginine, asparagine, histidine, leucine, serine, glycine, glutamic acid, phenylalanine and alanine.

15. The peptide analogue of claim 1 wherein the analogue is twelve amino acids.

16. The peptide analogue of claim 1 wherein the analogue is fifteen amino acids.

17. The peptide analogue of claim 1 wherein the altered amino acid(s) are altered to a non-conservative amino acid.

18. The peptide analogue of claim 1 wherein the N-terminal and C-terminal amino acids of the peptide analogue are D-amino acids.

19. A peptide analogue of 10 to 25 amino acids comprising at least ten contiguous amino acids selected from residues corresponding to 521–535 of SEQ. ID. NO:2, wherein two to five amino acids from those residues corresponding to 521–535 are altered to an amino acid other than the amino acid present in the native protein at that position, and wherein the peptide analogue competes for binding with the native GAD peptide to MHC and does not stimulate proliferation of GAD-reactive T-cells.

20. A peptide analogue of 7 to 25 amino acids comprising at least seven contiguous amino acids selected from residues corresponding to 521–535 of SEQ. ID. NO: 2, wherein one to three amino acids selected from the group consisting of arginine at position 525, lysine at position 528, proline at position 531 and lysine at position 534 are altered to an amino acid other than the amino acid present in the native protein at that position, and wherein the peptide analogue competes for binding with the native GAD peptide to MHC and does not stimulate proliferation of GAD-reactive T-cells.

21. The peptide analogue according to any one of claims 19 to 20 wherein the altered amino acid(s) are altered to an amino acid selected from the group consisting of arginine, asparagine, histidine, leucine, serine, glycine, glutamic acid, phenylalanine and alanine.

22. The peptide analogue according to any one of claims 19 to 20 wherein the N-terminal amino acid of the peptide analogue is a D-amino acid.

23. The peptide analogue according to any one of claims 19 to 20 wherein the peptide analogue is fifteen amino acids.

24. The peptide analogue according to any one of claims 19 to 20 wherein the peptide analogue is twelve amino acids.

25. The peptide analogue according to any one of claims 19 to 20 wherein one to five of the altered amino acids is altered to a non-conservative amino acid.

26. The peptide analogue according to any one of claims 19 to 20 wherein the N-terminal amino acid and the C-terminal amino acid are altered to a D-amino acid.

27. A pharmaceutical composition comprising a peptide analogue according to any one of claims 1–20 in combination with a physiologically acceptable carrier or diluent.

28. A peptide analogue of 7 to 25 amino acids comprising at least seven contiguous amino acids selected from residues corresponding to 521–535 of SEQ. ID. NO: 2, wherein one to five amino acid from those residues corresponding to 521–535 is altered to an amino acid other than the amino acid present in the native protein at that position, and the N-terminal amino acid and the C-terminal amino acid of the peptide analogue are altered to another amino acid, such that upon administration of the peptide analogue in vivo proteolysis is reduced, and wherein the peptide analogue competes for binding with the native GAD peptide to MHC and does not stimulate proliferation of GAD-reactive T-cells.

* * * * *